US010742811B2

(12) United States Patent
Ghai et al.

(10) Patent No.: US 10,742,811 B2
(45) Date of Patent: Aug. 11, 2020

(54) SMART COMMUNICATIONS AND ANALYTICS LEARNING ENGINE

(71) Applicants: Dharmendra Sushilkumar Ghai, Ulhasnagar (IN); Najat Abdulraheem, Doha (QA)

(72) Inventors: Dharmendra Sushilkumar Ghai, Ulhasnagar (IN); Najat Abdulraheem, Doha (QA)

( * ) Notice: Subject to any disclaimer, the term of this patent is extended or adjusted under 35 U.S.C. 154(b) by 0 days.

(21) Appl. No.: 16/191,139

(22) Filed: Nov. 14, 2018

(65) Prior Publication Data

US 2019/0356778 A1 Nov. 21, 2019

Related U.S. Application Data

(60) Provisional application No. 62/703,723, filed on Jul. 26, 2018, provisional application No. 62/728,503, filed on Sep. 7, 2018.

(30) Foreign Application Priority Data

May 16, 2018 (IN) .............................. 201811018345

(51) Int. Cl.
| H04M 1/64 | (2006.01) |
| H04M 3/51 | (2006.01) |
| G16H 40/20 | (2018.01) |
| G16H 10/60 | (2018.01) |
| G16H 80/00 | (2018.01) |

(52) U.S. Cl.
CPC .......... *H04M 3/5158* (2013.01); *G16H 10/60* (2018.01); *G16H 40/20* (2018.01); *G16H 80/00* (2018.01); *H04M 3/5166* (2013.01); *H04M 3/5183* (2013.01); *H04M 2203/558* (2013.01)

(58) Field of Classification Search
CPC ................................................... H04M 3/5158
USPC ........... 379/88.18; 705/2, 7.12; 1/1; 455/413
See application file for complete search history.

(56) References Cited

U.S. PATENT DOCUMENTS

| 6,246,871 B1 * | 6/2001 | Ala-Laurila .......... H04M 3/382 455/413 |
| 8,620,683 B2 * | 12/2013 | Findlay ............... G06F 19/3418 705/2 |
| 9,603,523 B2 * | 3/2017 | Dziubinski ......... G06F 19/3418 |

(Continued)

*Primary Examiner* — Md S Elahee
(74) *Attorney, Agent, or Firm* — Blank Rome LLP

(57) ABSTRACT

A healthcare patient appointment management system for managing patient appointments. The system includes an interactive voice response (IVR), teleconsult module, and SMS messaging system. The IVR module calls a patient, and solicits patient responses to confirm a patient appointment. The teleconsult module provides a teleconsultation with the patient. And the SMS messaging system provides SMS messages to the patient. A controller is in communication with the IVR module, teleconsult module, and SMS messaging system. The controller receives the patient responses from the interactive voice response module and determines if the patient confirmed the patient appointment. If the controller determines that the patient does not confirm the patient appointment, then the controller sends an SMS message to the patient via the SMS messaging system. The SMS message includes a link to conduct the teleconsultation with the patient and a healthcare provider via the teleconsult module.

20 Claims, 3 Drawing Sheets

(56) References Cited

U.S. PATENT DOCUMENTS

| | | | | |
|---|---|---|---|---|
| 2001/0037219 | A1* | 11/2001 | Malik | G06F 19/3418 |
| | | | | 705/2 |
| 2005/0283384 | A1* | 12/2005 | Hunkeler | G06F 19/324 |
| | | | | 705/2 |
| 2006/0173708 | A1* | 8/2006 | Vining | A61B 5/0002 |
| | | | | 705/2 |
| 2012/0253868 | A1* | 10/2012 | Ach | G06Q 10/06 |
| | | | | 705/7.12 |
| 2014/0156290 | A1* | 6/2014 | Kozicki | G06Q 30/0631 |
| | | | | 705/2 |
| 2017/0324684 | A1* | 11/2017 | Dharmapalan | H04L 51/04 |

* cited by examiner

SMART COMMUNICATIONS AND ANALYTICS LEARNING ENGINE

RELATED APPLICATION

The present application claims priority to Indian Patent Application No. 201811018345, filed May 16, 2018, U.S. Provisional Application No. 62/703,723, filed Jul. 26, 2018, and U.S. Provisional Application No. 62/728,503, filed Sep. 7, 2018. The entire contents of those applications are hereby incorporated by reference.

FIELD OF THE INVENTION

The present invention relates to information communication and technology in healthcare.

BACKGROUND OF THE INVENTION

Healthcare has come of age. The industry has grown in double digits over the last decade, due to the over-growing population. The population curve has seen an upward trend when it comes to the geriatric population. This class is usually dependent on the working or philanthropic class for all their needs including healthcare.

Though healthcare has shown a significant growth, the providers haven't been able to do much to fill up for patient no-show. Missed medical appointments not only disrupt schedules, but also leave doctors and nurses with gaps during the workday. In addition to this, it also creates financial burden for the providers.

No-show appointments represent a major burden on health care systems and have a negative impact on patient care. For instance, patient no-shows can cause scheduling and operational difficulties for clinics leading to reduced productivity. No-shows can also reduce access to care, as well as interrupt continuity of care and effective disease management for patients. Although the level of economic impact differs according to the size and nature of the healthcare organization, the overall financial cost of no-shows is substantial.

According to a 2016 study published in Multidisciplinary Digital Publishing Institute (MDPI), Basel by the journal Healthcare, it was estimated that the financial cost to the United Kingdom National Health Service (from nonattendance at outpatient clinics) was approximately 790 million Euros per year. Similarly, the Veterans Health Administration (VHA), one of the largest integrated healthcare delivery systems in the United States, estimates the cost of no-shows and unused appointments to be approximately $564 million annually. Likewise, a quality improvement project aimed to reduce the 'no show' rate in a Pediatric Neurology Clinic at Hamad General Hospital, Qatar conducted in 2016 highlights that 49 percent of patients referred to pediatric neurology did not show up for their appointments leading to long waiting times for new patients, and a waste of clinic resources. The same study underlines that the international bench-mark for primary care clinics is 5-10 percent, however for specialist healthcare centers, the no-show rate has been reported to be higher. This has created a dent in the pockets of the healthcare providers leading to wasted resources.

In addition, the nature of patients with respect to the use of technology has also to some extent hampered patient engagement and activation. As the providers' quest for population health management (PHM) focus finally shifts towards patient engagement, there has been growing interest from data/analytics firms, payers, telecom and device makers, and non-healthcare tech giants in bringing out user-friendly tools and apps. While this is being done, it's become challenging to understand where things are in terms of the adoption and impact of clinical patient engagement technology. Though telemedicine has been around for some time now, the use and spread has been very limited.

SUMMARY OF THE INVENTION

Accordingly, it is an object of the invention to provide an IVR that confirms a patient appointment. It is a further object of the invention to provide a teleconsult for connecting a patient to a healthcare provider. It is a further object of the invention to integrate an IVR system with a teleconsult system to provide teleconsultation once a patient cancels or re-schedules an appointment.

In accordance with these and other objects of the invention, a healthcare patient appointment management system for managing patient appointments. The system includes an interactive voice response (IVR), teleconsult module, and SMS messaging system. The IVR module calls a patient, and solicits patient responses to confirm a patient appointment. The teleconsult module provides a teleconsultation with the patient. And the SMS messaging system provides SMS messages to the patient. A controller is in communication with the IVR module, teleconsult module, and SMS messaging system. The controller receives the patient responses from the interactive voice response module and determines if the patient confirmed the patient appointment. If the controller determines that the patient does not confirm the patient appointment, then the controller sends an SMS message to the patient via the SMS messaging system. The SMS message includes a link to conduct the teleconsultation with the patient and a healthcare provider via the teleconsult module.

DETAILED DESCRIPTION OF THE INVENTION

Figure 1:
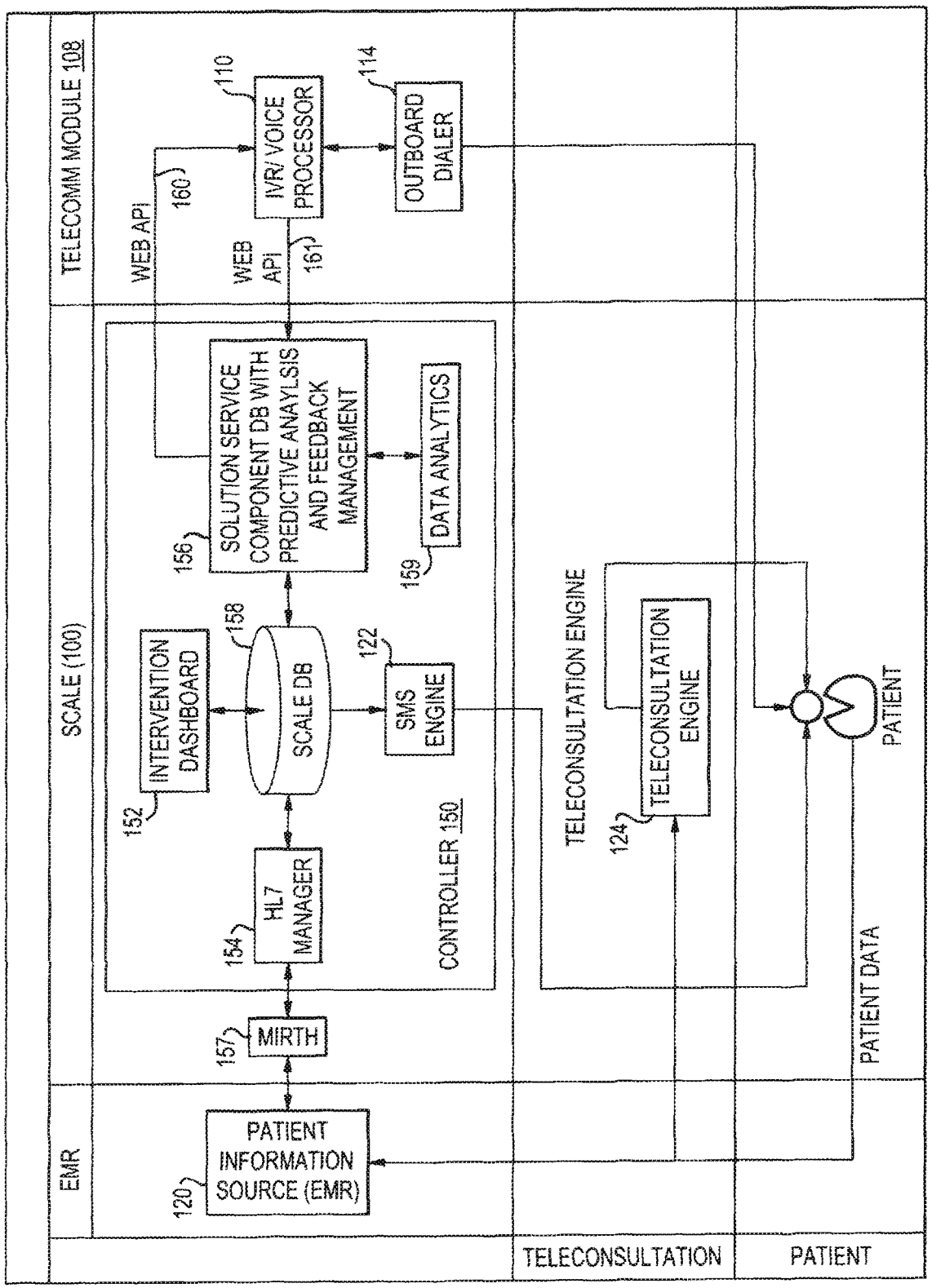
FIG. 1 is a block diagram of one embodiment of the invention.

In describing the illustrative, non-limiting preferred embodiments of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. Several preferred embodiments of the invention are described for illustrative purposes, it being understood that the invention may be embodied in other forms not specifically shown in the drawings.

Turning to the drawings, FIG. 1 shows the Smart Communications and Analytics Learning Engine (SCALE) system 100 in accordance with the present invention. The SCALE 100 can include an EMR (Electronic Medical Records) module 120, SMS (Short Message Service) engine 122, IVR 110, and Controller 150. However, though the EMR module 120, teleconsultation engine 124 and IVR 110 need not be integral with the SCALE 100, but instead can be separate and in communication with the SCALE 100. The Controller 150 is in communication with the EMR 120, SMS 122, and IVR 110.

The SCALE 100 operates with a Telecom module 108. The Telecom module 108 includes an Interactive Voice Response (IVR)/Voice processor 110 and an associated outbound dialer 114. The IVR/voice processor 110 has the functionality required to program the interactive communication plan during a call, such as language based voice scripts with dynamic data filling in the blanks in preconfigured sentences as voice scripts and also has the functionality to accept integrations with API based data. The outbound dialer 114 calls the patients, and passes the control once connected back to the IVR 110.

The Controller 150 includes a Dashboard 152, an HL7 Manager 154, Solution Service Component 156, database 158, SMS engine 122 and data analytics 159. The Dashboard 152 is the web-based view for the application's working and configurations. The HL7 manager 154 is the universal HL7 integration platform, and includes a cross-platform HL7 interface 157, such as Mirth which is currently owned by Quality Systems. The Solution service component 156 is the web API used to connect the controller 150 to the IVR 110. The SMS 122 is the engine used to generate and send SMS text messages to patients. The dashboard 152, HL7 Manager 154, Solution Service component 156, database 158 and data analytics 159 are in communication with one another within the Controller 150.

In operation, the EMR 120 contains all patient data and appointment data and can be represented by any of the myriad of EMR systems available in the market. The HL7 Manager 154 receives data from the EMR 120 in the form of HL7 messages via the Mirth interface 157. The type of HL7 message used is Scheduling Information Unsolicited (SIU) and Patient Administration Admission/Discharge/Transfer (ADT) messages. SIU messages are part of the HL7 standard, and include information about appointments. The appointment data is in the SIU messages and the Patient Data is in the ADT message, and they are linked to each other via a unique patient identifier. The ADT message has the necessary information to identify an existing or a new patient along with his/her demographic detail and the SIU message has appointment related information for a particular patient. The ADT and SIU messages contain the following fields in Table 1:

TABLE 1

| SIU Message (Appointment Data) | ADT Message (Patient Data) |
| --- | --- |
| Message header segment | Set ID - Patient ID |
| Schedule Activity Information | Patient ID (External ID) |
| Notes and comments segment | Patient ID (Internal ID) |
| PATIENT | Alternate Patient ID |
| Patient Identification | Patient Name |
| Patient visit | Mother's Maiden Name |
| Patient visit - additional information | Date of Birth |
| Observation segment | Sex |
| Diagnosis | Patient Alias |
| RESOURCES | Race |
| Resource Group | Patient Address |
| SERVICE | County Code |
| Appointment Information - Service | Phone Number - Home |
| Notes and comments segment | Phone Number - Business |
| GENERAL RESOURCE | Primary Language |
| Appointment Information - General Resource | Marital Status |

TABLE 1-continued

| SIU Message (Appointment Data) | ADT Message (Patient Data) |
| --- | --- |
| Notes and comments segment | Religion |
| LOCATION RESOURCE | Patient Account Number |
| Appointment Information - Location | SSN Number - Patient |
| Notes and comments segment | Driver's License Number |
| PERSONNEL RESOURCE | Mother's Identifier |
| Appointment Information - Personnel Resource | Ethnic Group |
| Notes and comments segment | Birth Place |
|  | Multiple Birth Indicator |
|  | Birth Order |
|  | Citizenship |
|  | Veterans Military Status |
|  | Nationality Code |
|  | Patient Death Date and Time |
|  | Patient Death Indicator |

The data from the EMR 120 includes Patient Appointment and demographics data noted in Table 1 above. The appointment data is picked, processed and inserted into the database 158. The process involves storing raw information received in the HL7 messages and then using that to generate intelligent second order data as reorganized by the solution service 156 and where required, transformed data for the solution service component into a part of the SCALE DB 158

With the help of the Mirth interface 157, these HL7 messages are inserted into staging tables in the SCALE database 158, the staging tables save the data obtained from the EMR 120 and keep track of the original data received from the EMR. The staging tables can be stored, for example, at the database 158. There are two staging tables for entering data, namely Patient Staging data and Appointment Staging data. The tables contain the following data shown in Table 2:

TABLE 2

| Patient Staging | Appointment Staging |
| --- | --- |
| table unique ID | table unique ID |
| Internal Id | Placer Appointment ID |
| Hospital code | Registration No |
| Registration Date Time | Hospital code |
| Title | Doctor ID |
| First name | Doctor Name |
| Middle Name | Speciality Code |
| Last Name | Speciality Description |
| Full Name | Service Type |
| Is New Born Flag | Hospital Location |
| Mothers Maiden Name | Clinic ID |
| Father or Husband Name | Clinic Name |
| Date Of Birth | Date of Appointment |
| Sex | Appointment From Date Time |
| Marital Status | Appointment To Date Time |
| Spouse Name | Appointment Status |
| Occupation | Appointment Type ID |
| Guardian | Appointment Duration |
| Guardian Relationship | Appointment Duration Unit |
| Guardian Address | Event Reason |
| Guardian Phone | Filler Contact Person |
| Guardian Cell No | Remarks |
| Guardian Email | Process Status |
| Age type | Last Update Datetime |
| Age | Additional Info1 |
| Address1 | Additional Info2 |
| Address2 | Additional Info3 |
| Patient Locality | Additional Info4 |
| Patient Other Locality | Additional Info5 |
| Patient City | Sent |
| Patient State | Date of Booking |
| Patient Country | Visited Flag |

TABLE 2-continued

| Patient Staging | Appointment Staging |
| --- | --- |
| Patient PostalCode | |
| Patient Phone | |
| Patient cellno | |
| Patient EMail | |
| Religion | |
| Nationality | |
| InsuranceCompany | |
| PatientType | |
| Qualification Id | |
| DOB | |
| Deleted | |
| Hospital Location | |
| Last Updated Datetime | |
| source of information | |
| NationalId | |
| AlternateID | |
| AlternateIDType | |
| Language | |
| Ethinic Group | |
| Race | |
| Death Flag | |
| Death Date Time | |
| Additional Info1 | |
| Additional Info2 | |
| Additional Info3 | |
| Additional Info4 | |
| Additional Info5 | |
| Firstname_Alias | |
| MiddleName_Alias | |
| LastName_Alias | |
| IsSent | |

When sending data from the database 158 to the IVR 114, patient demographic information stored at the database 158 is added to the staging table to provide the information shown in Table 2. That data can include ADT (e.g., sex, date of birth) from Table 1, and also other data (such as table ID, Appointment) stored at the database 158 associated with the patient's ID from the appointment detail Table 1.

The columns of Table 2 are then transformed by the solution service component 156. This is done by a scheduled task in the solution service component 156 which transforms the data. For example, the data from the MIRTH 157 can be stored in the database 158 and then the solution service 156 can retrieve that data and transform it. Alternatively, the data from the MIRTH 157 can be transformed at the HL7 Manager 154 and then stored in the database 158. In the process of transformation, the following tasks are done. Data in the staging tables (Table 2) is a raw feed of data from the EMR 120, and hence has some repeating entries for patients who have come before or for other masters representing patient/appointment information which have been captured and uniquely identified earlier.

The solution service component 156 references the master tables of fields in Table 3, which is stored in the database 158, to find existing unique entries, and if these entries aren't already present in the staging data, they are added to the masters in the scale DB 158. Master data is the data which is required frequently in multiple locations. For example, Nationality in patient Demographics, we have Patients with Qatari as their Nationality, instead of having "Qatari" in each row of patient data we save reference to the master table, having all the nationalities in One place.

For example, suppose that Qatari as a nationality does not exist in the Database 158. When the data is being transformed by the solution service component 156 and it encounters a patient with a Qatari nationality, it would be added to the master table. This way a clean de-duplicated and normalized data set is maintained in the SCALE DB 158. The clean, normalized data set forms the basis for the applications smooth functioning and also the data analytics engine 159. Some other columns necessary for the application flow are added.

TABLE 3

| Masters updated |
| --- |
| Hospital code |
| Title |
| Marital Status |
| Occupation |
| Guardian Relationship |
| Age type |
| Patient Locality |
| Patient Other Locality |
| Patient City |
| Patient State |
| Patient Country |
| Patient Postal Code |
| Religion |
| Nationality |
| Patient Type |
| Language |
| Ethnic Group |
| Sex |
| Clinic Name |
| Appointment Status |
| Service Type |
| Appointment Duration Unit |

TABLE 4

| Data sent to IVR |
| --- |
| Appointment ID |
| Registration No |
| Date Of Booking |
| Appointment Duration |
| Patient Name |
| Patient Name Alias (Arabic Name) |
| Sex |
| Marital Status |
| Age |
| Patient Country |
| Patient Cell No |
| AlternatePhone |
| National Id (Qatar ID) |
| Language |
| appointment Code |
| Hospital Facility |
| Clinic Name |
| Doctor Name |
| Speciality |
| Service Type |
| Year of Birth |
| Appointment Day of the week |
| Appointment From time |
| Appointment to time |

The Solution component 156 takes the second order data (Table 4) from the database 158 and makes it available to the IVR 110. This information exchange happens on a programmed frequency initiated by the IVR 110 as a Web API request 160, the data is fetched according to the configurations saved in solution service component 156, such that a subset of patient appointments reaches the IVR 110. The subset contains relevant patients who should receive calls on the day when data is fetched. These patients e.g. can be the ones who have appointments the following day and also those who have appointments 3 days later, and this is a configuration in the system to have various combinations of these patients.

The IVR 110 then makes the outbound dialer 114 call the patient's phone number to confirm that the patient will attend the scheduled appointment. For instance, the IVR 110 retrieves the patient's identifying information (Table 4) from the subset of patients whose appointments fall on the days which are selected through the configurations in the business logic fetched immediately prior to its schedule from Scale DB 158, to call the patient through outbound dialer 114. The IVR 110 also uses the appointment information (Table 4) saved in Scale DB 158 to question whether the patient will attend the appointment.

The invention can use any suitable IVR 110 to confirm the patient appointment. The patient is guided through the call and responses are recorded. For example, the IVR 110 can trigger the dialer 114 to dial the patient using the patient's telephone number in the patient data and to record the patient's responses. The patient response data is saved to the system, such as at the IVR 110 and also is sent using a Web API call 161, to the solution service component 156 and then stored at the database 158. Subsequently the information of appointment confirmation is sent to the EMR 120 via the HL7 manager 154, using an appropriate HL7 message which is freshly constructed and sent back to the EMR 120. The HL7 message back to the EMR 120, i.e. SIU messages are generated to update the Appointment statuses back in the EMR 120. The messages may be SIU-S15—Notification of appointment cancellation, SIU-S14—Notification of appointment modification or other messages from the HL7 standard can be generated according to the business requirements.

Figure 3:
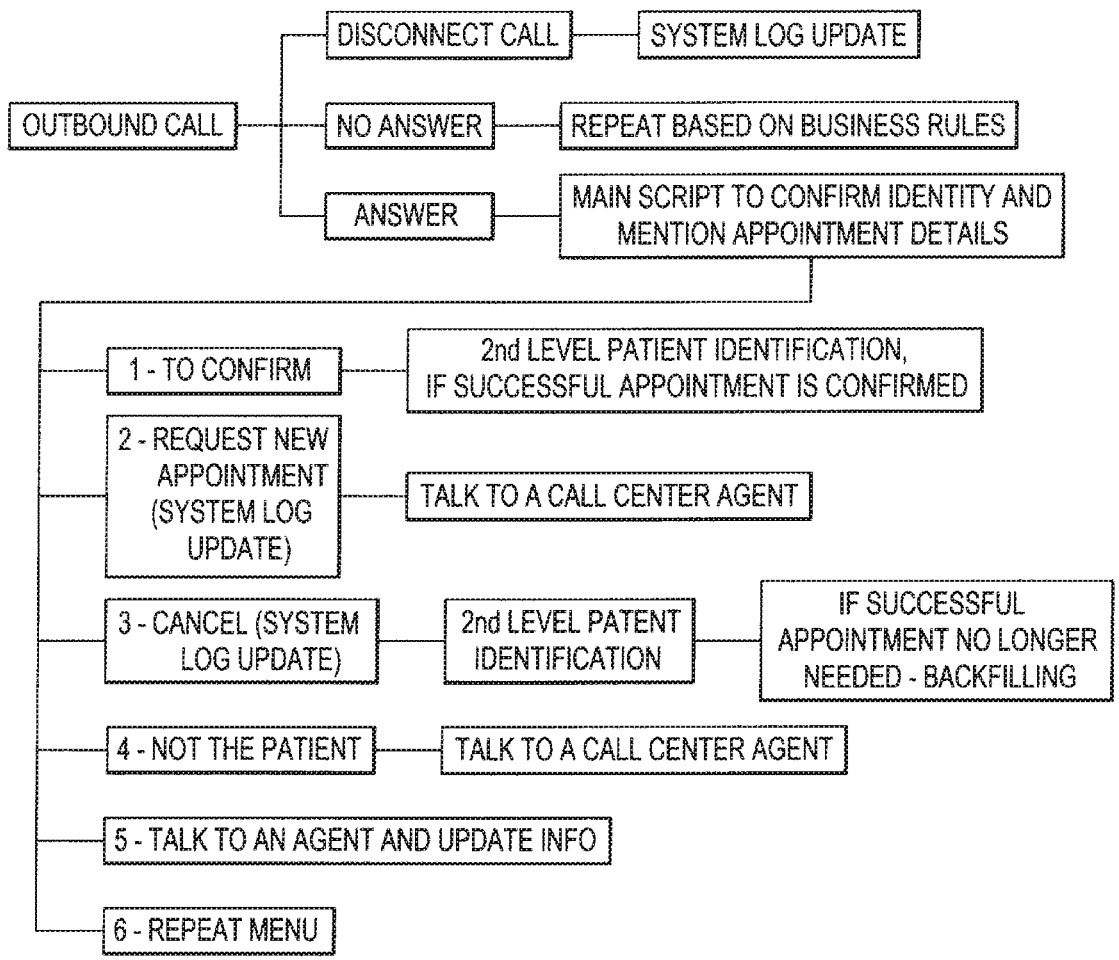
FIG. 3 is a flow diagram showing operation of the IVR in accordance with one embodiment of the invention.

Referring to FIGS. 1, 3, the solution service component 156 receives the patient response data and determines if the user confirms the appointment, requests a new appointment, or cancels the appointment. If the user cancels the appointment or re-schedules the appointment, the solution service component 156 triggers the generation of a text message to the patient having the link for a video teleconsultation request. For example, an SMS text message can be sent to the patient via SMS messenger 122, though any suitable messaging system can be utilized such as an email generator. To do so, the solution service component 156 retrieves the patient's SMS number (e.g., cell phone number, Patient Name, appointment date-time) from the SCALE DB 158, the SIU message. The data retrieved can vary depending on the SMS message to be sent to the user.

The solution service component 156 then sends a control signal to the SMS engine 122 to generate an SMS message. The SMS is generated using a standard text message template, to the patient, with suitable information including a web link (URL) for launching a Video Conference (VC) application. For example, the solution service component 156 receives the responses from the call manager 110, associated with patient identifying information (e.g., at least a patient ID and the responses to the questions as listed above). The solution service component 156 determines that the patient has cancelled the appointment, retrieves contact information from the database 158 associated with the patient ID, and generates a text message to send to the patient. The solution service component 156 then queues up the text message for transmitting to the linked phone number for the SMS engine 122, which in turn transmits the message to the patient.

The patient can then access the text message at his/her mobile device, and click on the VC link, which in turn launches a VC mobile or desktop application that initiates a teleconsultation with a healthcare provider (e.g., physician, nurse, pharmacy, etc.). In one embodiment, the message can be generic and lack any specific content for that particular patient, who can then set the parameters for the teleconsultation, for example, by selecting a healthcare provider. In another embodiment, the link can be customized to the patient so that the teleconsultation is established with the patient's own physician, as is provided in the patient identifying information already retrieved from the EMR 120 and available as data in the SCALE database 158.

When the patient clicks on the link, the teleconsultation is established. A URI (Universal Resource Identifier) is generated using the VC Application Programming Interface (API). The URI creates a unique code that helps connect the two parties. The URL contains an identifier uniquely identifying the patient party and it may or may not contain a provider identifying identifier based on the use case as described above.

The present invention addresses the current problems with access to healthcare. More specifically, the present invention provides increased access to healthcare through IVR managed tele-consultation. The present invention expands the access to tele-health, and introduces a one-of-its-kind Smart Communications Analytics learning Engine (SCALE) 100, a one-size-fits-all engine. This platform merges with IVR 110, tele-consultation 124 and analytics 159 to offer healthcare services.

Figure 4:
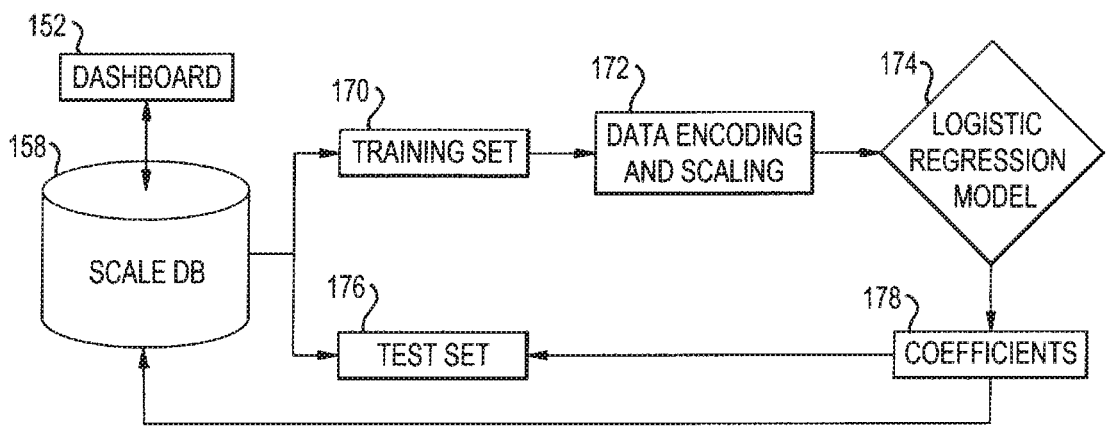
FIG. 4 is a flow diagram showing the operation of the data analytics engine

Referring to FIG. 4, the analytics and predictive module 159 performs analytics on the patient appointment details data, which is then passed to a predictive model that calculates the likelihood of a patient showing up for an appointment. This is the primary purpose of this component such that user agents looking at the dashboard are shown a single score of the "likelihood" of the patient showing up, the importance of which has been emphasized in the introduction of this application as "no-shows" contributing to a tremendous burden on the healthcare delivery system. The predictive model works on logistic regression. The data from Table 2 is passed to an R-script, which does splits into two parts as training 170 and testing 176 datasets in a ratio of 70:30. This a form of supervised learning, where we first train the algorithm with the help of the training set. Then this trained algorithm (in this case Logistic Regression) is applied to the test set, where the results are validated.

The training dataset 170 includes all the data where the status of the patient visit is known. For data encoding, the data is categorized into categorical data and numerical data, the categorical data is encoded 172 so that logical calculations can be made on it, the process of encoding involves changing the categories to numerical IDs. The numerical data is scaled using the standard Scaling function in R.

The encoded and scaled data is then fitted into a logistic regression model 174.

$$Z_i = \ln\left(\frac{P_i}{1-P_i}\right) = \alpha + \beta_1 x_1 + \ldots + \beta_n x_n$$

Logistic Regression Model algorithm 174

By using GLM library in R we fit the dataset into the above algorithm. Where a and R are coefficients to be calculated from the equation. On fitting the equation with the R, the logistic regression gives out the coefficient values for each of the components supplied to the model. Here, R is an open source programming language used for data modelling (predictive analysis) and related statistical functions, and is used to generate the predictive model here. It includes a library of tools to fit various use cases, and in one embodiment an integrated development environment is used called R Studio and a library called GLM for predictive modeling of the show/no-show probability.

The mechanism of predictive modelling is a mathematical model evaluated such that, all parameters influencing a complex real-world outcome are validated to be influencers, given suitable weightage and mathematical coefficients are derived which in turn are used to do predictions for unknown outcomes. This is tested on the test data 176 to validate results and accuracy of the model. After the model has been trained the same logistic regression is applied to a dataset of unknown results where we predict out the probability of a patient coming to an appointment.

The accuracy of the model increases with the number of items in the training set which is obtained through Scale DB 158. This is a learning engine and the accuracy of the model improves over time with increasing volume of data. This engine keeps running, repeatedly on a configured frequency and generates its model and coefficients, using the data in the SCALE DB 150. A web service from the application dashboard calls the service to calculate the probability when the admin user opens the dashboard 152, Admin user will be able to see the predictive score for each patient in a tabular format in the dashboard 152. For example the predictive scoring can be used to set priorities of the calling dataset and determine the sequence in which the calls are made based user configuration where either least likely to show up are called earlier or vice-versa. The data analytics can be done, for example, at regular intervals (daily/hourly, etc.) by the data analytics engine 159, and/or upon user request.

The Solution service component 156 is able to use Business rules (which define how the application works and changes in different scenarios) configured using the dashboard 152, and stored in the SCALE DB 150, stating how the solution should work, e.g. how IVR response codes should be configured, which day's appointment should be picked and others listed later in the document. The business logics are written in the core part of the application (Solution service component 156), for e.g. the web service or the HL7 Manager according to the different scenarios. The IVR 110 includes automatic dialer 114 functionality to reach the correct patient followed by validation of identity once identified. An example of a sample call flow is shown in FIG. 3. The present invention provides teleconsultation 124 through the IVR 110, where the maximum effort that goes in is just a phone call away and healthcare is delivered in real time at the patient's doorstep.

As illustrative, non-limiting examples, the invention is particularly well-suited to patients that have difficulty leaving the home or who has frequent visits to the healthcare provider, such as for example, a patient who has undergone a back surgery, is too aged to move out alone, an infant is under the weather or have to complete office task and traveling would take time. The SCALE 100 takes care of this by connecting the patient to the healthcare professional. All the user has to do is follow a simple step. The user uses a smart phone 10 (FIG. 2) to call a number, or to receive an automated call by the IVR. The Interactive Voice Response (IVR) 110 instructs the user to follow instructions. For example, press 1 to confirm the scheduled appointment with the healthcare provider, 2 to tele-consult or 3 to cancel. The user then chooses the desired option. If the user chooses option 2 on the IVR 110, it confirms the appointment time for tele-consulting, and the user confirms the time by pressing the selected option.

The call ends after providing the IVR 110 with the response. The user then receives an access code as text message on the user's mobile number along with the link to download the VC (Video Conference) application, which is a telehealth mobile smartphone application that operates on the user's smartphone. The VC app extracts the information from the Electronic Medical Record 120 that has been linked to the patient's unique identification number. An EMR view is a standardized view of the existing EMR solution which the provider uses for getting informed about clinical details of the patient (patient electronic medical record) from his earlier encounters.

The Access code identifies the context between applications. The Access code has a context of an appointment for an encounter in the VC (VSee) application, connecting a provider and a patient at a certain time slot (scheduled) using the access code. No other information is shared. No other information is extracted from EMR using this automation. The provider can evaluate the EMR of the patient which he will do using his existing EMR access screen which is familiar to him with based on the identification context of the patient visible to him in the scheduled slot while doing the consult in VSee. EMR review would be seamless without excessive/potentially incomplete data transfer between applications.

Figure 2:
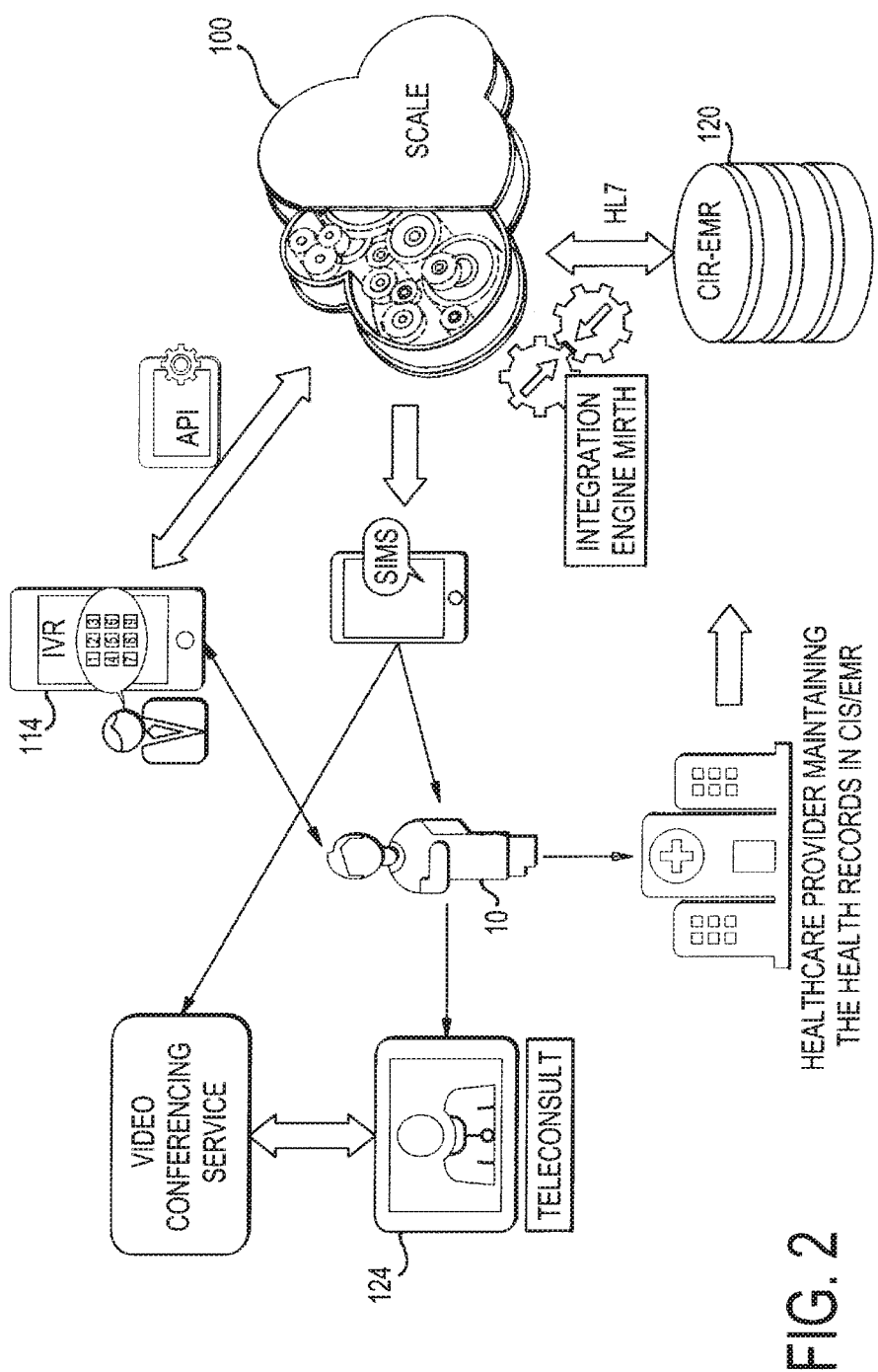
FIG. 2 is an information flow diagram of the invention.

Referring to FIG. 2, a patient using a portable processing device 10, such as a smart phone, is linked to his/her healthcare provider organization, who in-turn keeps his electronic medical record up-to-date in an enterprise EMR/CIS (Electronic Medical Record/Clinical Information System) 122. The EMR data can also be shared with a remote server, such as at a healthcare center (physician's office, hospital, etc.), or somewhere else. The EMR data includes the patient's disease profile and clinical findings as well as scheduled future appointments. SCALE 100 picks up the appointments and convert them to tasks for an automated dialer through an IVR (Interactive voice response) engine 110 to call each patient and attempt to get a confirmation for appointments. The patient confirms the appointment and proceeds to their appointments at the physical clinic assigned to that encounter.

Alternatively, the patient can cancel or choose to reschedule for personal reasons or limitations of not having support at home on that day or being too aged or fragile to move. Such patients and re-scheduling requests put pressure on the stretched resources of clinics and providers and make it difficult for patients to get their necessary follow-up encounters. Extending IVR 110 tools to send teleconsultation 124 links on SMS when such patients need them to schedule and start a teleconsult encounter is a paradigm shift in chronic care management and follow up for extremes of age.

The text based link described takes into consideration the requirement of data protection and privacy of the patient such that only the identifiers of patient go to the provider, while the patient gets a link to download and be ready for a teleconsult session on the VC application, or if the application is already downloaded, be straightaway ready for a teleconsult session.

Patient EMR is confidential information which only is designated provider should have access to, and to achieve this care must be taken that this information accidently does not go to other possible viewers. The solution described, ensures that the clinical record stays in the EMR 120 and does not need to flow to either the SCALE 150 or the IVR 110 or the Teleconsult 124, however on use of the solution the patient is identified correctly and linked to the correct physician, who in-turn is able to view the EMR by virtue of his inherent tools and credentials in existing EMR view screens, because the patient identifier information flows through to him using the EMR→HL7→WebApi→IVR→Call flow→Response Webapi→SMS→VC described above.

In the embodiment of the invention, confidential clinical information is prevented from being exchanged between the IVR system 110 and the teleconsult system 124 however the flow of information between the patient and provider is managed during the teleconsult session itself. i.e. The provider, who is one side of this session, is from the organization providing care to the patient and has access to the patient, once the system identifies the correct patient, the provider will be able to review his records on his familiar CIS/EMR screens. The patient who is the other side of this session, needs identification and validation, a function which is done by the IVR integration such that the patient is able to confirm his identity during the call (refer to the call flow above).

To conduct the teleconsult 124, the user logs in with their user ID and password, at the scheduled time to get medical advice from the user's physician or specialist. The SCALE 100 provides tele-consultation through a teleconsult 124 that is user friendly with minimal assistance for the geriatric population, and any suitable teleconsult 124 can be utilized. It is available at a significant speed even on a low bandwidth with optimum clarity. It is a safe and secure engine when it comes to user data, while being HIPAA compliant. A patient who is on the extremes of age and requires assistance to get to a follow up consult can be limited by availability of family support, time and energy on maintaining his healthcare visit schedules. Chronic disease management especially requires multiple visits to the clinic for regular follow up. The Teleconsult option is really helpful for this, however with the challenges around getting the right information to clinician for managing the case effectively require VC integration with CIS/EMR.

Thus, teleconsultation is provided without the need of moving private clinical data from one system to another. As the medical professional has already access to the EMR (120) where all the patient's medical information is stored. Thus, the controller 150 need not send any information directly to the teleconsult engine 124. Small interventions such as patient identification, provider identification & teleconsult order identification using the unique code in the message, the message when decoded by the VC application extracts the relevant data (User ID of the Patient, User ID of Doctor, Appointment date-time) and does the needful for a provider to access the correct record when the teleconsult is ongoing.

Patients' access to teleconsult has traditionally had a need for specific training of how to get to the platform on the day of the consult or even to plan for a future consult. This problem is solved by the present invention. Once the user selects via the IVR 110 to conduct a teleconsultation, the Controller 150 sends a message to the patient device 10, such as an SMS text via SMS 122. The SMS text includes a link that, when selected by the patient, launches a teleconsult (i.e., videoconferencing). The teleconsult 124 automatically connects the patient with a healthcare provider (such as a physician). No data is transferred to the healthcare provider for data security, as the healthcare provider can access the EMR from their device.

Data Source (e.g., EMR 120)

The EMR 120 can be a system including a processing device and storage device such as a database that stores EMR data. The EMR data includes all the scheduled appointments for a date in the future as decided by business rules. The Controller 150 can transmit reminders to patients for their appointments via the user's smartphone application 10. The data dump is captured in a RDBMS by the user's smartphone application. For example, the data input may come from a MIRTH application with Staging Tables (Table 2) linked to it for various HL7 messages 157.

In one example embodiment, the following data can be stored at the EMR 120: Patient Appointment Data (SIU), Patient Data (ADT), and Master Fields. The Patient Appointment Data can include, for example, data related to healthcare appointments, such as the date and time of all healthcare appointments associated with a particular patient. The patient is identified by his/her unique ID and the appointment of the patient is identified by the appointment ID and the entire session is managed by tracking these unique identifiers. That data can be used for a variety of purposes, for example the Controller 150 can use the Patient Appointment Data to generate a periodic update that is sent to the patient for future appointments.

Any update in the patient information (Table 2) is received as HL7 message and the relevant updates are done in the database 158. The Master fields (containing master related to all Patient Appointment Data, Patient Data) are updated or added as the case may be during the process of data transformation.

Data Transformation in Data Collected from EMR to Patient Connect DB

In the process of transformation, the following tasks are done. The master tables of fields followed below are checked, if there is any data with same name the ID is picked up and updated in the main tables. If the data is not found, a new row is inserted into the tables, other columns necessary for the application flow are added, thereby ensuring that a clean and unique data set is maintained for all master lists.

Web Services Request 160 to IVR

Web services 160 sends and receives data to and from the IVR 110 and updates the responses in the database 158. A web API request 160 is sent to the IVR system 110, with all the necessary fields to make a call to the Patient. According to the Business rule configuration the data will be pulled for the patient whose appointment falls on Current date+N days. All the data will be passed on to the web service 160 and then to IVR 110. This request can be sent both as a single item or pooled together. After request has been sent the necessary status will be updated.

IVR Response 161

After the IVR has processed the call progress data, the IVR 110 would be aware of the response status from the call, 161. These statuses can include, for example, the following: Confirm appointment, Cancel appointment, Reschedule appointment, Not the patient, No answer, Verification failed, Forwarded to Call center. This information linked to patient identifier will be sent back to the solution service component 156 using a web API response 161.

Any response will be processed by the solution service component 156 according to the response status master, preconfigured using dashboard 152 into the SCALE DB 150. The data can be received in the following forms: The Web Services Response 161 is received by the web services and will trigger different events. For Confirmed and Cancelled appointment HL7 messages would be generated via HL7 Manager 154. Any other status would be saved in the database.

HL7 Manager 154

In the case of response from the IVR being confirmed or cancelled Appointment, the appointment details are generated by the solution service component 156 and sent to the EMR 120 Using the HL7 Manager 154. The HL7 manager 154 makes HL7 messages for the scenarios. These messages are then picked up by the Mirth, which is a cross-platform HL7 interface engine that enables bi-directional sending of HL7 messages between systems. The Mirth 157, processes the HL7 messages and sends them to the EMR database 120.

Configurations

The application will have configurations so that the admin users can manage the application Flow. The following configurations would be included, for example: Current Date+N Day(s), IVR response master, SMS Event Configuration.

The Current Date+N Days configuration manages the appointment date(s) to be picked and sent to the IVR. There may be multiple configurations where user can enter the day to be picked. For example, a user may add both +3 days and +5 Days. Then the application would pick the appointment on 3rd day and 5th day from the server date-time.

For the IVR response master, the IVR 110 will give multiple responses to the application. To manage this master would be created. The master can have 3 editable Columns: Status Name, IVR Response Code, and ID. The admin user can to map the IVR response codes to the Statuses in the Patient Connect DB.

The SMS Event Configuration, the event based SMS would be sent by the application to the patients. The admin user can toggle these events so that Patient can receive the SMS notification. The SMS event includes, for example, Confirmed appointment, Cancelled Appointment, SMS with URL to download teleconsultation software if the patient wishes to initiate tele consultation. The URL link will have app download location and the unique clinic code. The on-duty physicians attached to the clinic code who will receive the call and accept the call to initiate consultation.

SMS Service 122

The event based SMS is added to a table based upon the SMS Configurations. The events can be configured according to business needs, e.g. if the patient cancels their appointment, the solution service component 156 can generate a message, which can be sent to the user using the SMS engine 122. The invention provides predictive, pre-emptive and personalized care. This smart technology model is a long-term data strategy amid an industry-wide sea. Available legacy IT systems have a lack of interoperability. The present invention provides IVR, tele-consultation and analytics 159 to help the providers achieve tangible business and clinical benefits.

The invention stores, processes and acts on the information fed in it that is helpful both to the patients and the doctors. The present invention makes it easy to make advanced clinical decisions and reduce preventable adverse effects, which in turn frees up the physicians' time for more personalized care, enabling effective time management. The system allows to identify preferred mode of consultation a specific population type, by ethnicity or disease type prefers. It also allows the right kind of engagement and outreach.

Accordingly, the present invention brings together IVR, virtual consultation and analytics on a single platform, which adds value to healthcare delivery and patient engagement in a simple technical solution manageable by an aging population. By providing a direct link between the IVR and virtual consultation, the patient can seek intervention through a virtual consultation. The system enables physicians to reach patients through teleconsultation who might otherwise not know that teleconsultation is available or appropriate for their illness. And the invention solves the difficult technical task of establishing a teleconsultation by providing the patient with a simple link to initiate the teleconsultation session. It further provides the patient with an alternative of using teleconsultation rather than rescheduling a personal appointment, which can take longer to obtain.

The system and method of the present invention include operation by one or more processing components or devices, including a mobile device, mobile application and server. For example, the controller 150 can be a processing device that performs the operation of the dashboard 152, HL7 manager 154, and solution service 156, and can also optionally the EMR 120, SMS 122, teleconsult 124, IVR 110 and outbound dialer 114. Or a separate processing device can be provided for each of the controller 150, HL7 manager 154, and solution service 156, as well as the EMR 120, SMS 122, teleconsult 124, outbound dialer 114 and IVR 110.

It is noted that the processing device can be any suitable device, such as a computer, server, mainframe, processor, microprocessor, PC, tablet, smartphone, or the like. Thus, for example, the IVR 110 and the VC/teleconsult 124 can each be on the same or different servers. The processing devices can be used in combination with other suitable components, such as a display device (monitor, LED screen, digital screen, etc.), memory or storage device, input device (touchscreen, keyboard, pointing device such as a mouse), wireless module (for RF, Bluetooth, infrared, WiFi, etc.). The information may be stored on a computer hard drive, on a CD ROM disk or on any other appropriate data storage device or medium, which can be located at or in communication with the processing device.

The operation of the processing device(s) is implemented by computer software that permits the accessing of data from an electronic information source. The software and the information in accordance with the invention may be within a single, free-standing computer or it may be in a central computer networked to a group of other computers or other electronic devices. The information may be stored on a computer hard drive, on a CD ROM disk or on any other appropriate data storage device. The system can also be implemented on the cloud and comprise a cloud computing system which provide access via the Internet to shared computing resources, such as servers, storage devices, networks, and/or applications on demand or in real time without regard to the location of those resources.

Thus as used herein, the computing system or processing device includes a single electronic computing device that includes, but is not limited to a single computer, virtual machine, virtual container, host, server, laptop, and/or portable device or to a plurality of electronic computing devices working together to perform the function described as being performed on or by the computing system. And a medium includes one or more non-transitory physical media that together store the contents described as being stored thereon. Embodiments may include non-volatile secondary storage, read-only memory (ROM), and/or random-access memory (RAM). And an application includes one or more computing modules, programs, processes, workloads, threads and/or a set of computing instructions executed by a computing system. Example embodiments of an application include software modules, software objects, software instances and/or other types of executable code.

The entire process is conducted automatically by the processor, and without any manual interaction. Accordingly, unless indicated otherwise the process can occur substantially in real-time without any delay or manual action.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A healthcare patient appointment management system for managing patient appointments, the system comprising:
   an interactive voice response module configured to call patients and solicit patient responses to confirm patient appointments;
   a virtual teleconsult system configured to provide a virtual teleconsultation with patients;
   a messaging system configured to provide messages to patients; and
   a controller in communication with the interactive voice response module, the virtual teleconsult system, and the messaging system, the controller;
      receiving patient appointment data from a patient information source and storing the patient appointment data in a database;
      receiving patient admission, discharge, or transfer (ADT) data from the patient information source and storing the patient ADT data in the database;
      using the patient appointment data and the patient ADT data to instruct the interactive voice response module to call patients and solicit patient responses to confirm patient appointments;
      receiving the patient responses from the interactive voice response module and determining if patients confirm patient appointments;
      in response to a determination that a patient did not confirm a patient appointment, using the patient appointment data and the patient ADT data to construct a link to a virtual teleconsultation with a healthcare provider via the virtual teleconsult system and using the patient appointment data and the patient ADT data to construct a message to the patient that includes the link to the virtual teleconsultation;
      outputting an instruction to the messaging system to output the message that includes the link to the patient.

2. The system of claim 1, further comprising the patient information source.

3. The system of claim 1, wherein the controller does not receive clinical data from the patient information source.

4. The system of claim 1, wherein the messaging system comprises a short message service (SMS) text messaging system.

5. The system of claim 1, wherein the messaging system comprises an email system.

6. The system of claim 1, wherein the controller provides at least some of the patient appointment data or the patient ADT data to the teleconsult system.

7. The system of claim 1, wherein the controller constructs the link such that the teleconsult system establishes a virtual teleconsultation between the patient and the healthcare provider scheduled to attend the patient appointment.

8. The system of claim 1, wherein the controller operates the interactive voice response module based on the patient appointment data or the patient ADT data.

9. The system of claim 1, wherein the controller formats the message based on the patient appointment data or the patient ADT data.

10. The system of claim 9, wherein the controller retrieves patient contact information from the patient appointment data or the patient ADT data and formats the message for delivery to the patient contact information.

11. The system of claim 1, wherein the controller formats the virtual teleconsultation based on the patient appointment data or the patient ADT data.

12. The system of claim 1, wherein the teleconsult system connects the patient with the healthcare provider but does not provide any patient clinical data to the healthcare provider.

13. The system of claim 1, wherein the virtual teleconsult system comprises a mobile smartphone application that operates on a user's smartphone.

14. The system of claim 11, the message further including an access code.

15. A method for managing patient appointments using a healthcare patient appointment management system, the method comprising:
   receiving patient appointment data from a patient information source and storing the patient appointment data in a database;
   receiving patient admission, discharge, or transfer (ADT) data from the patient information source and storing the patient ADT data in the database;
   calling patients using an interactive voice response module to solicit patient responses to confirm patient appointments;
   determining, at a controller based on the patient responses, whether patients confirm patient appointments;
   in response to a determination that a patient did not confirm a patient appointment;
      using the patient appointment data and the patient ADT data to construct a link to a virtual teleconsultation with a healthcare provider via a virtual teleconsult system;
      using the patient appointment data and the patient ADT data to construct a message to the patient that includes the link to the virtual teleconsultation;
      outputting an instruction to a messaging system to output the message that includes the link to the patient.

16. A healthcare patient appointment management system for managing patient appointments, the system comprising:
   a database that stores patient appointment data and patient admission, discharge, or transfer (ADT) data received from a patient information source;
   a controller that:
      using the patient appointment data and the patient ADT data to instruct an interactive voice response module to call patients and solicit patient responses to confirm patient appointments;
      receives the patient responses from the interactive voice response module and determines if patients confirm patient appointments;
      in response to a determination that a patient did not confirm a patient appointment, uses the patient appointment data and the patient ADT data to construct a link to a virtual teleconsultation with a healthcare provider via a virtual teleconsult system and uses the patient appointment data and the patient ADT data to construct a message to the patient that includes the link to the virtual teleconsultation;
      outputs an instruction to a messaging system to output the message that includes the link to the patient.

17. The system of claim 16, wherein the message is a text message or an email.

18. The system of claim 16, wherein the controller constructs a link to conduct a virtual teleconsultation with a healthcare provider scheduled to attend the patient appointment.

19. The system of claim 14, wherein the database does not store patient clinical data.

20. The system of claim 16, wherein the link establishes a virtual teleconsultation between the patient and a healthcare provider but does not provide patient clinical data to the healthcare provider.

* * * * *